US007888435B2

(12) United States Patent
Lichtenhan et al.

(10) Patent No.: US 7,888,435 B2
(45) Date of Patent: Feb. 15, 2011

(54) PROCESS FOR CONTINUOUS PRODUCTION OF OLEFIN POLYHEDRAL OLIGOMERIC SILSESQUIOXANE CAGES

(75) Inventors: Joseph D. Lichtenhan, Petal, MS (US); Sukhendu Bikash Hait, Hattiesburg, MS (US); Joseph J. Schwab, Huntington Beach, CA (US); Michael J. Carr, Hattiesburg, MS (US)

(73) Assignee: Hybrid Plastics, Inc., Hattiesburg, MS (US)

( * ) Notice: Subject to any disclaimer, the term of this patent is extended or adjusted under 35 U.S.C. 154(b) by 1108 days.

(21) Appl. No.: 11/420,449

(22) Filed: May 25, 2006

(65) Prior Publication Data

US 2006/0263318 A1 Nov. 23, 2006

Related U.S. Application Data

(63) Continuation-in-part of application No. 11/371,195, filed on Mar. 7, 2006, now Pat. No. 7,485,692, and a continuation-in-part of application No. 11/342,240, filed on Jan. 27, 2006, now Pat. No. 7,638,195, which is a continuation-in-part of application No. 11/225,607, filed on Sep. 12, 2005, now Pat. No. 7,553,904, which is a continuation-in-part of application No. 11/166,008, filed on Jun. 24, 2005, now abandoned, which is a continuation of application No. 09/631,892, filed on Aug. 4, 2000, now Pat. No. 6,972,312, and a continuation of application No. 10/351,292, filed on Jan. 23, 2003, now Pat. No. 6,933,345, which is a continuation-in-part of application No. 09/818,265, filed on Mar. 26, 2001, now Pat. No. 6,716,919, said application No. 11/166,008 is a continuation of application No. 09/747,762, filed on Dec. 21, 2000, now Pat. No. 6,911,518, and a continuation of application No. 10/186,318, filed on Jun. 27, 2002, now Pat. No. 6,927,270.

(60) Provisional application No. 60/684,666, filed on May 25, 2005, provisional application No. 60/659,722, filed on Mar. 7, 2005, provisional application No. 60/608,582, filed on Sep. 10, 2004, provisional application No. 60/147,435, filed on Aug. 4, 1999, provisional application No. 60/351,523, filed on Jan. 23, 2002, provisional application No. 60/192,083, filed on Mar. 24, 2000, provisional application No. 60/171,888, filed on Dec. 23, 1999, provisional application No. 60/301,544, filed on Jun. 27, 2001, provisional application No. 60/648,327, filed on Jan. 27, 2005.

(51) Int. Cl.
C08G 77/20 (2006.01)

(52) U.S. Cl. ...................... 525/474; 528/34

(58) Field of Classification Search ................ 525/474; 528/34
See application file for complete search history.

(56) References Cited

U.S. PATENT DOCUMENTS

| 2,801,968 | A | 8/1957 | Furby et al. |
|---|---|---|---|
| 3,231,499 | A | 1/1966 | Smith |
| 3,247,111 | A | 4/1966 | Oberright et al. |
| 3,267,031 | A | 8/1966 | Buehler |
| 3,278,436 | A | 10/1966 | Dazzi et al. |
| 3,280,031 | A | 10/1966 | Brennan et al. |
| 3,292,180 | A | 12/1966 | Axworthy |
| 3,340,286 | A | 9/1967 | Schiefer et al. |
| 3,347,791 | A | 10/1967 | Thomson et al. |
| 3,390,168 | A | 6/1968 | Brown |
| 3,673,226 | A | 6/1972 | Malec |
| 4,381,396 | A | 4/1983 | Ryang |
| 4,483,107 | A | 11/1984 | Tomoyori et al. |
| 4,513,132 | A | 4/1985 | Shoji et al. |
| 4,657,965 | A | 4/1987 | Watanabe et al. |
| 4,900,779 | A | 2/1990 | Leibfried |
| 4,946,921 | A | 8/1990 | Shirata et al. |
| 5,008,360 | A | 4/1991 | Bard et al. |
| 5,034,490 | A | 7/1991 | Jacobine et al. |
| 5,047,491 | A | 9/1991 | Saho et al. |
| 5,047,492 | A | 9/1991 | Weidner et al. |
| 5,190,808 | A | 3/1993 | Tenney et al. |
| 5,194,489 | A | 3/1993 | Frances et al. |
| 5,412,053 | A | 5/1995 | Lichtenhan et al. |
| 5,484,867 | A | 1/1996 | Lichtenhan et al. |
| 5,589,562 | A | 12/1996 | Lichtenhan et al. |
| 5,830,950 | A | 11/1998 | Katsoulis et al. |
| 5,858,544 | A | 1/1999 | Banaszak Holl et al. |
| 5,939,576 | A | 8/1999 | Lichtenhan et al. |
| 5,942,638 | A | 8/1999 | Lichtenhan et al. |
| 6,075,068 | A | 6/2000 | Bissinger |
| 6,100,417 | A | 8/2000 | Lichtenhan et al. |
| 6,228,904 | B1 | 5/2001 | Yadav et al. |

(Continued)

FOREIGN PATENT DOCUMENTS

EP 0624591 11/1994

(Continued)

OTHER PUBLICATIONS

Marsmann et al., Cage-rearrangement of Silsesquioxanes, Polyhedron, vol. 16, No. 19, pp. 3357-3361, 1997.

Chevaliaer and Mackinnon, Ring-Opening Olefin Metathesis Polymerisation (ROMP) as a Potential Cross-Linking Mechanism for Siloxane Polymers, Journal of Inorganic and Organometallic Polymers, vol. 9, No. 3, 1999.

(Continued)

*Primary Examiner*—Kuo-Liang Peng
(74) *Attorney, Agent, or Firm*—David H. Jaffer; Pillsbury Winthrop Shaw Pittman LLP

(57) ABSTRACT

Methods for continuous bulk production of polyolefin polyhedral oligomeric silsesquioxanes and their amino, isocyanate, and alcohol derivatives using silane coupling agents as precursors.

8 Claims, 3 Drawing Sheets

U.S. PATENT DOCUMENTS

| | | |
|---|---|---|
| 6,245,849 B1 | 6/2001 | Morales et al. |
| 6,245,926 B1 | 6/2001 | Charrin et al. |
| 6,252,030 B1 | 6/2001 | Zanket et al. |
| 6,329,490 B1 | 12/2001 | Yamashita et al. |
| 6,770,724 B1 | 8/2004 | Lichtenhan et al. |
| 2005/0010012 A1* | 1/2005 | Jost et al. .................... 528/34 |

FOREIGN PATENT DOCUMENTS

| WO | WO 01/10871 | 2/2001 | |
|---|---|---|---|
| WO | 03 042223 | * | 5/2003 |

OTHER PUBLICATIONS

Haddad, T.S., et al., Hybrid, Norbornenyl-Based Polyhedral Oligosilsesquioxane (POSS) Polymers, J. Am. Chem. Soc. Polym. Preprints. Jan. 1997. vol. 38, No. 1.pp. 127-128.

Mather, P.T. et al., Mchanical Relaxation and Microstructure of Poly (norbornyl-POSS) Copolymers. Macromolecules. Feb. 1999. vol. 32. pp. 1194-1203.

* cited by examiner

PROCESS FOR CONTINUOUS PRODUCTION OF OLEFIN POLYHEDRAL OLIGOMERIC SILSESQUIOXANE CAGES

RELATED APPLICATIONS

This application claims the benefit of U.S. Provisional Patent Application Ser. No. 60/684,666 filed May 25, 2005, and is a continuation-in-part of U.S. patent application Ser. No. 11/371,195 filed Mar. 7, 2006 now U.S. Pat. No. 7,485,692 (which claims the benefit of U.S. Provisional Patent Application No. 60/659,722 filed Mar. 7, 2005) and a continuation-in-part of U.S. patent application Ser. No. 11/342,240 filed Jan. 27, 2006 now U.S. Pat. No. 7,638,195 (which claims the benefit of U.S. Provisional Patent Application Ser. No. 60/648,327 filed Jan. 27, 2005), which is a continuation-in-part of U.S. patent application Ser. No. 11/225,607 filed Sep. 12, 2005 now U.S. Pat. No. 7,553,904 (which claims priority from U.S. Provisional Patent Application Ser. No. 60/608,582 filed Sep. 10, 2004), which is a continuation-in-part of U.S. patent application Ser. No. 11/166,008 filed Jun. 24, 2005, now abandoned which is (a) a continuation of U.S. patent application Ser. No. 09/631,892 filed Aug. 4, 2000, now U.S. Pat. No. 6,972,312 (which claims priority from U.S. Provisional Patent Application Ser. No. 60/147,435, filed Aug. 4, 1999); (b) a continuation of U.S. patent application Ser. No. 10/351,292, filed Jan. 23, 2003, now U.S. Pat. No. 6,933,345 (which claims priority from U.S. Provisional Patent Application Ser. No. 60/351,523, filed Jan. 23, 2002), which is a continuation-in-part of U.S. patent application Ser. No. 09/818,265, filed Mar. 26, 2001, now U.S. Pat. No. 6,716,919 (which claims priority from U.S. Provisional Patent Application Ser. No. 60/192,083, filed Mar. 24, 2000); (c) a continuation of U.S. patent application Ser. No. 09/747,762, filed Dec. 21, 2000, now U.S. Pat. No. 6,911,518 (which claims priority from U.S. Provisional Patent Application Ser. No. 60/171,888, filed Dec. 23, 1999); and (d) a continuation of U.S. patent application Ser. No. 10/186,318, filed Jun. 27, 2002, now U.S. Pat. No. 6,927,270 (which claims priority from U.S. Provisional Patent Application Ser. No. 60/301,544 filed Jun. 27, 2001). The disclosures of the foregoing applications are incorporated herein by reference.

FIELD OF THE INVENTION

This invention relates generally to the methods and compositions of olefin containing polyhedral oligomeric silsesquioxanes (POSS). More specifically, it relates to methods for the continuous bulk production of polyvinyl POSS and derivative chemical products.

BACKGROUND OF THE INVENTION

Recent developments in nanoscience have enabled cost effective manufacture of commercial quantities of polyhedral oligomeric silsesquioxanes that are best described as nano-structured chemicals due to their precise chemical formula, hybrid (inorganic-organic) chemical composition, large physical size relative to the size of traditional chemical molecules (0.3-0.5 nm), and small physical size relative to larger-sized traditional fillers (>50 nm).

The commodity nature of organosilane coupling agents makes them highly desirable for use as starting materials for nanoscopic POSS molecules. Prior art has taught the use of silane coupling agents in the formation of POSS cages (U.S. Pat. No. 6,972,312) and in the functionalization of POSS cages with reactive groups (U.S. Pat. No. 6,927,270).

This invention teaches continuous production methods for olefin bearing POSS and in particular vinyl POSS cages. This advancement was needed as vinyl silanes are the lowest cost reactive silane coupling agent and because vinyl POSS cages are highly desirable for chemical derivatization into other chemical groups. Applications for olefin POSS and its derivatives include improved composite resins, paints, coatings, adhesives, and surface properties, which lead to fire resistance, printability, biocompatibility, and permeability controlled, high Tg and heat distortion materials, glassification agents, printing aids, and nanofiltration materials.

SUMMARY OF THE INVENTION

The present invention describes methods of continuous synthesis of polyolefin containing polyhedral oligomeric silsesquioxanes. It also describes compositions of chemicals derived from them.

The preferred compositions herein contain olefin functionalities on nanostructured chemicals and nanostructured oligomers (FIG. 1). The nanostructured chemical classes include polyhedral oligomeric silsesquioxanes, polysilsesquioxanes, polyhedral oligomeric silicates, polysilicates, polyoxometallates, carboranes, boranes, and polymorphs of carbon. Chemical derivatives from olefin containing POSS have been prepared by hydrosilation, phosphorylation and thiolation (U.S. Pat. No. 5,939,576), epoxidation and oxidation methods (U.S. Pat. Nos. 5,942,638 and 6,100,417), crossmetathesis, Heck additions, Diels-Alder reactions, hydroformylation and Wacker oxidation. This invention describes polyisocyanate derivatives, dhydroamination and subsequent carboxylation. Polyalcohol derivatives are also described through ethylene and propylene oxide additions to olefinic POSS.

Polyfunctional POSS systems are of utility in the formation of cross-links in materials such as polycarbonate, polyesters, urethanes, epoxides, polyethers, polyamides, polyolefines, bismaleimides, chitin, cellulose, polyacids, and silicones.

Vinyl containing nanostructured chemicals are particularly effective in polymers as they control the motions of polymer chains, and segments, at the molecular level. Vinyl containing nanostructured chemicals as also highly desirable in cosmetics, adhesives, paints, coatings and dyes as the impart unique surface and physical properties. The incorporation of a nanostructured chemical into a polymer favorably impacts a multitude of polymer physical properties. Properties most favorably improved are heat distortion and flammability characteristics. Other properties improved include time dependent mechanical and thermal properties such as creep, compression set, shrinkage, modulus, and hardness. In addition to mechanical properties, other physical properties are favorably improved, including lower thermal conductivity, gas oxygen barrier and permeability, surface gloss and color. In addition, vinyl containing nanostructured chemicals are highly useful for surface glassification and for chemical derivitization. These improved properties may be useful in a number of applications, including composite materials and durable coatings.

DEFINITION OF FORMULA REPRESENTATIONS FOR NANOSTRUCTURES

For the purposes of understanding this invention's chemical compositions the following definition for formula representations of Polyhedral Oligomeric Silsesquioxane (POSS) and Polyhedral Oligomeric Silicate (POS) nanostructures is made.

Polysilsesquioxanes are materials represented by the formula $[RSiO_{1.5}]_x$ where x represents molar degree of polymerization and R=represents organic substituent (H, siloxy, cyclic or aliphatic or olefininc, or aromatic groups that may additionally contain reactive functionalities such as alcohols, isocyanates, esters, amines, ketones, olefins, ethers or halides or which may contain fluorinated groups). Polysilsesquioxanes may be either homoleptic or heteroleptic. Homoleptic systems contain only one type of R group while heteroleptic systems contain more than one type of R group.

POSS and POS nanostructure compositions are represented by the formula:

$[(RSiO_{1.5})_n]_{\Sigma\#}$ for homoleptic compositions $[(RSiO_{1.5})_n(R'SiO_{1.5})_m]_{\Sigma\#}$ for heteroleptic compositions (where R≠R')

$[(RSiO_{1.5})_n(RXSiO_{1.0})_m]_{\Sigma\#}$ for functionalized heteroleptic compositions (where R groups can be equivalent or inequivalent)

In all of the above R is the same as defined above and X includes but is not limited to OH, Cl, Br, I, alkoxide (OR), acetate (OOCR), peroxide (OOR), amine (NR$_2$) isocyanate (NCO), and R. The symbols m and n refer to the stoichiometry of the composition. The symbol Σ indicates that the composition forms a nanostructure and the symbol # refers to the number of silicon atoms contained within the nanostructure. The value for # is usually the sum of m+n, where n ranges typically from 1 to 24 and m ranges typically from 1 to 12. It should be noted that Σ# is not to be confused as a multiplier for determining stoichiometry, as it merely describes the overall nanostructural characteristics of the system (aka cage size).

DETAILED DESCRIPTION OF THE INVENTION

The present invention teaches a continuous process for the manufacture of olefinic containing nanostructured chemicals and chemical derivatives from them that are useful as building blocks for the reinforcement of polymer coils, domains, chains, and segments at the molecular level in thermoset and thermoplastic resins, oil or aqueous emulsions, latexes, and suspensions.

Figure 1:
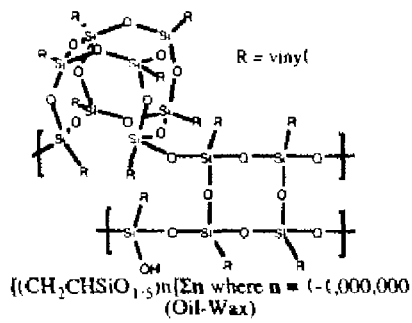
FIG. 1 shows examples of polyvinyl containing POSS nanostructured chemicals.
Figure 1:
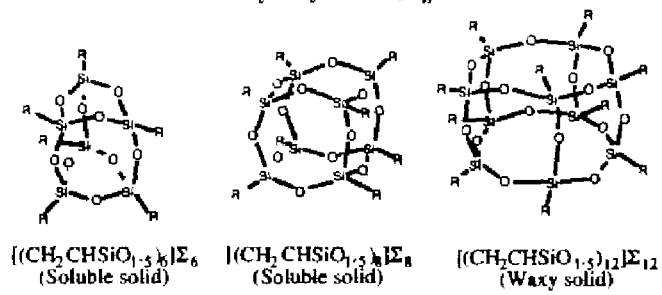
Figure 1:
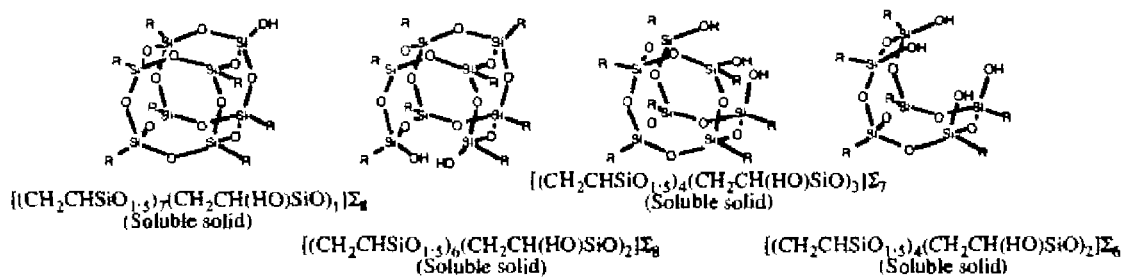
Figure 1:
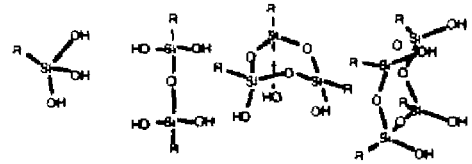

Nanostructured chemicals, such as the olefin POSS structures illustrated in FIG. 1, can exist as solids, waxes, and oils. A variety of olefiinc R groups such as cyclohexene, norbornene, allyl, and styrenyl can be considered for inclusion on nanostructured chemicals. However, the lowest cost systems that are also commercially available commercially are the vinylsilanes. Vinyltrialkoxysilanes and vinyltrichorosilane are commercially available in industrial quantities. Historically the synthesis process for vinyl POSS systems has been plaqued by low yields, long reaction times, and irreproducible product yields. The chemical equation for synthesis of vinyl POSS involving trichloro or alkoxy silanes can be generically represented as follows:

$$ViSiCl_3 + H_2O \rightarrow vinylPOSS + HCl \quad (1)$$

$$ViSi(OR)_3 + H_2O + HCl \rightarrow vinylPOSS + ROH \quad (2)$$

$$ViSiCl_3 + MeOH \rightarrow vinylPOSS + HCl \quad (3)$$

The chemical reactions illustrated in Equations 1, 2, and 3 are shown in nonstoichiometric form as the effects of water, HCl, ROH (alcohol), and concentration of silane have dramatic influences on product yield and the purity of isolated product. A wide variety of olefin POSS structures can be obtained as illustrated in FIG. 1.

Figure 2:
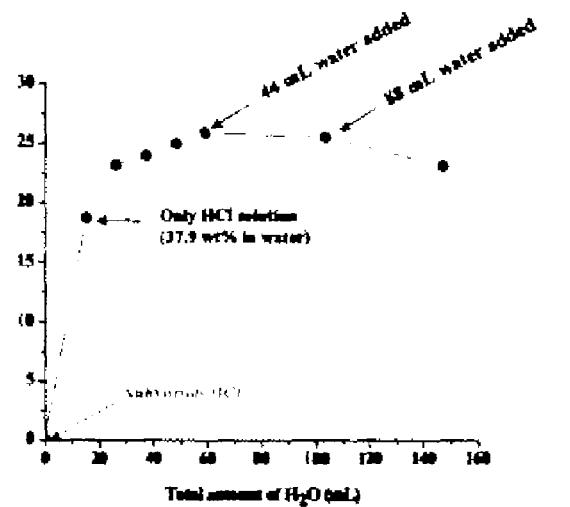
FIG. 2 illustrates the effect of water on yield of octavinyl POSS.
Figure 3:
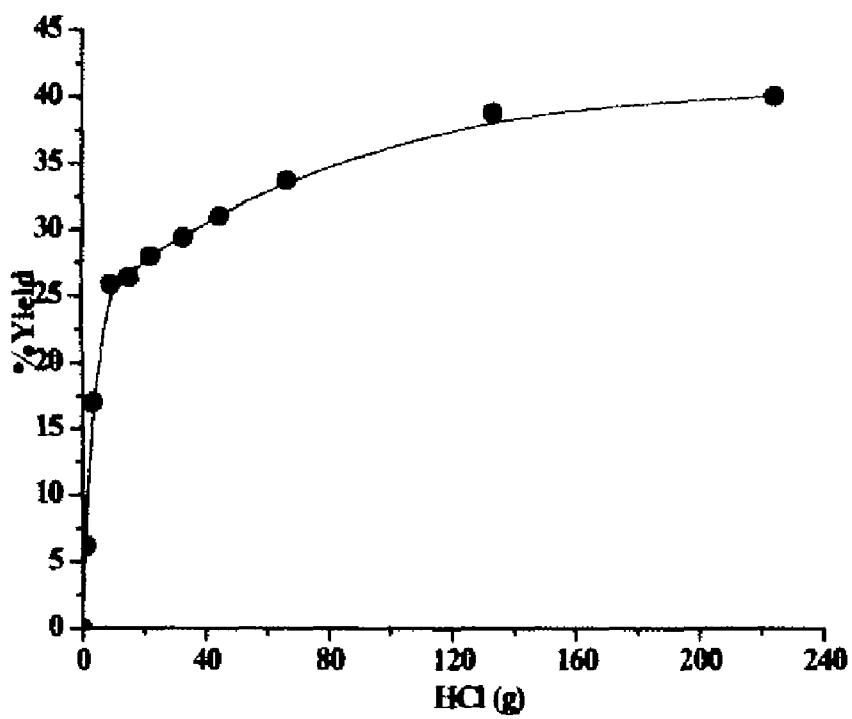
FIG. 3 illustrates the effect of acid on yield of octavinyl POSS.
Figure 4:
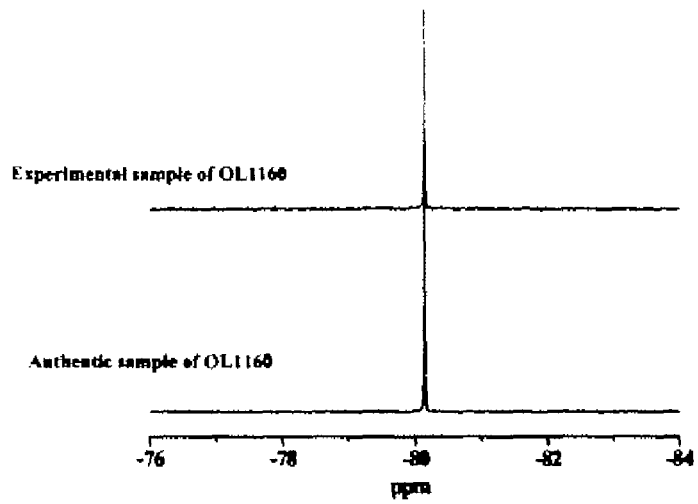
FIG. 4 shows $^{29}$Si NMR spectra of batch vs continuously produced octavinyl POSS.

To illustrate this point, FIGS. 2 and 3 describe the complex relationship of water and acid relative to yield of the vinyl POSS cage. Furthermore, the concentration of the acid in equations 2 and 3 can be varied from 1% to 39% with a preferred concentration of 37.9%.

In the design of a continuous process it is also desirable to recognize the chemical stability and the ability to isolate the olefin POSS products from the reaction medium. In Equations 1-3, the vinyl POSS is both chemically stable to the reaction medium and insoluble. The insolubility of the POSS product, in the reaction medium, facilitates its collection via filtration of the reaction mixture. The collection of product is further facilitated by running the reaction at room temperature which avoids the loss of product due to reactions or solubilzation that can occur at elevated temperatures.

The concentration of silane added to the reaction medium can be varied from 0.01 M-5.0 M. A preferred concentration range is 0.3 M to 2.0 M, and a more preferred concentration for continuous reaction purposes is 1.3 M-1.5 M.

While a continuous process has been established for each reaction illustrated in Equations 1-3, equations 1 and 3 are less desirable, as they require equipment investments to handle corrosive HCl byproducts. Equation 2 is more easily managed though use of readily available plastic or glass lined reaction vessels and filtration equipment.

It should be further noted that equations 1 and 3 produce three equivalents of HCl for each equivalent of vinyltrichlorosilane while equation 2 produces three equivalents of alcohol per equivalent of vinyltrialkoxy silane. The liberation of alcohol in equation 2 is highly desirable as it aids in solubilization of the starting materials and in the solubilization of vinyl POSS intermediates and resinous by-products. In the case of equations 1 and 3, alcohol is required to rinse the final POSS products to remove such intermediates, oligomers and polymers.

Finally, the formation of vinyl POSS in equations 1-3 is driven by the precipitation of the product from the acid methanol solution. A resinous by-product is also produced in the reaction but it does not precipitate from the reaction as it remains soluble in methanol.

EXAMPLES

General Process Variables Applicable To All Processes

As is typical with chemical processes, there are a number of variables that can be used to control the purity, selectivity, rate and mechanism of any process. Variables influencing the process for the formation of nanostructured chemicals (e.g. POSS/POS, etc.) include the size, polydispersity, and composition of the nanostructured chemical desired, the kinetics, thermodynamics, and aids used during the reaction process such as catalysts, cocatalyst, supports, and surfactants, and other factors such as temperature, pressure, templates, solvent, gases and mixtures thereof.

Vinyl POSS can be produced from vinyltrimethoxy, vinyltriethoxy silane or vinyltrichloro silane (or related derivatives), either via the filtration of product every 24 hours or by filtration of the product after the addition of silane over a period of successive 24 hour additions. In general it is preferred to filter and collect the reaction product once every 24 hours.

Example 1

Vinyltrichorosilane Method

In the case of synthesis from vinyltrichloro silane, the vinyltrichloro silane is premixed for 10 minutes with 3.5 equivalents of methanol. The prereacted solution (0.85%) is then added to a stirred solution of methanol (65.7% v/v), HCl (32.7% v/v), and water (0.65% v/v). The periodic addition of a solubilizing amount of methanol is required to minimize the formation of a sticky white resinous by-product that can contaminate the octavinyl POSS. The amount of MeOH required is variable and is determined by visual solubilization of any sticky precipitated resin on the walls of the reaction vessel.

Example 1a

In a 1000 mL round bottom flask containing methanol (500 mL), HCl (250 ml), and water (5 mL) the mixture was allowed to come to room temperature. Vinyl trimethoxy silane (6.5 mL) was added slowly to the reaction mixture and reaction was continued for 24 hours with stirring (magnetic stirrer). In one case it was filtered and the reactor charged with additional silane (6.5 mL), and the process is repeated 5 to 20 times. 20 time addition and filtration produced 35.3% Vi8T8. (Yield was based on the final product, which was washed with methanol and dried.) 10 times addition and no filtration produces 32.8% Vi8T8. (Yield was based on the final product, which was washed with methanol and acetone and dried in vacuum).

Example 1b

In a 1000 mL round bottom flask containing methanol (500 mL), HCl (250 ml), and water (5 mL) added slowly, the mixture was allowed to come to room temperature. Vinyl trimethoxy silane (6.5 mL) was added slowly to the reaction mixture and reaction was continued for 24 hours with stirring (magnetic stirrer). Total yield of 5 times addition/filtration was 40.8%. Total yield of 5 times addition/no filtration was 40.8%. (Yield was based on the final product which was washed with methanol and dried)

Example 2

Vinyltrialkoxysilane Method

The process for producing octavinyl POSS from vinyltrimethoxy silane involves the room temperature addition of the silane (0.85% v/v) every 24 hours to a stirred solution of methanol (65.7% v/v), HCl (32.7% v/v), water (0.65% v/v). The reaction mixture is capable of continuously producing octavinyl POSS either via the successive filtration of product or by the continuous addition of silane.

Alternately, in a 1000 mL round bottom flask containing methanol (500 mL), HCl (250 ml), and water (5 mL) added slowly, the mixture was allowed to come to room temperature. Vinyl trimethoxy silane (6.5 mL) was added slowly to the reaction mixture and reaction was continued for 24 h with stirring (magnetic stirrer). In one case it was filtered and the reactor charged with additional silane (6.5 mL), and the process repeated 5 to 20 times. In another case the reactor was charged with additional silane (6.5 mL) and the process was repeated 5 to 20 times.

Example 3

Hydroamination of Vinyl POSS

Figure 5:
FIG. 5 illustrates the process of vinyl hydroamination.

The hydroamination of olefins is a well known reaction. FIG. 5 illustrates hydroamination of vinyl POSS. A 50 g sample of vinyl POSS is suspended in a liquid ammonia solution and to this $PtBr_2$ and $nBu_4PBr$ is added. The mixture was allowed to react over 8 hours to product the desired octaminoethyl POSS. The product was isolated as a white solid.

Example 4

Polyisocyanate Formation

Figure 6:
FIG. 6 illustrates the process of isocyanate formation.

A 50 g sample of octaminoethyl POSS was reacted with phosgene for 4 hours at 50° C. to produce the octaethylisocyante POSS. The product was isolated as a white solid. FIG. 6 illustrates polyisocyanate formation with POSS.

Example 5

Hydrolytic Oxidation of Vinyl POSS

Figure 7:
FIG. 7 illustrates the process of alcohol formation.

Transition metal oxides such as $OsO_4$ and $MnO_4^-$ have long been known to be powerful oxidizing agents. Amine catalyzed osmylation followed by hydrolysis is a known method to produce dialcohol products from vinyl groups. A 50 g sample of vinyl POSS was stirred into osmium tetroxide. The mixture was allowed to react for 2 hours and then washed with aqueous acid to produce a white solid of octaethylglycol POSS that was collected through filtration. FIG. 7 schematically shows the process of alcohol formation.

While certain representative embodiments and details have been shown for purposes of illustrating the invention, it will be apparent to those skilled in the art that various changes in the methods and apparatus disclosed herein may be made without departing from the scope of the invention which is defined in the appended claims.

What is claimed is:

1. A method for manufacture of an amine-bearing chemical comprising the steps of (a) mixing a silane coupling agent bearing an olefin with a chemical selected from the group consisting of polyhedral oligomeric silsesquioxanes and polyhedral oligomeric silicates in the presence of an acidic or basic catalyst, and water, to form an olefin-bearing chemical (b) collecting the olefin-bearing chemical through filtration, and (c) amination of the olefin-bearing chemical.

2. The method of claim 1, wherein a second silane coupling agent is used to incorporate a different functional group into the olefin-bearing chemical formed in step (a).

3. The method of claim 1, wherein the process is utilized in a continuous or batch manufacturing method.

4. The method of claim 1, wherein the reaction medium is not heated above 40° C.

5. The method of claim 1, wherein the olefin-bearing chemical is in a physical state selected from the group consisting of oils, amorphous, semicrystalline, crystalline, elastomeric, rubber, and crosslinked materials.

6. The method of claim 2, wherein the olefin-bearing chemical includes nonreactive R groups.

7. The method of claim 1, wherein the amination changes a physical property of the chemical selected from the group consisting of adhesion to a polymeric surface, adhesion to a composite surface, adhesion to a metal surface, water repellency, density, low dielectric constant, thermal conductivity, glass transition, viscosity, melt transition, storage modulus, relaxation, stress transfer, abrasion resistance, fire resistance, biological compatibility, gas permeability, and porosity.

8. The method of claim 1, wherein the olefin-bearing chemical formed in step (a) further includes an epoxy group.

* * * * *